United States Patent [19]

Mechoulam et al.

[11] 4,282,248
[45] Aug. 4, 1981

[54] PINENE DERIVATIVES AND PHARMACEUTICAL COMPOSITIONS CONTAINING THE SAME

[76] Inventors: Raphael Mechoulam, Tcheruichovsky 12, Jerusalem; Naphtali Lander, Even Gevirol 182, Tel-Aviv; Shabtay Dikstein, 7 Habanai St., Jerusalem, all of Israel

[21] Appl. No.: 59,859

[22] Filed: Jul. 23, 1979

[30] Foreign Application Priority Data

Aug. 2, 1978 [IL] Israel ................................. 55274

[51] Int. Cl.³ ................ A61K 31/22; A61K 31/05; C07C 69/013; C07C 39/17
[52] U.S. Cl. ................................. 424/299; 424/346; 560/141; 560/255; 568/734
[58] Field of Search ................ 560/141, 255; 568/734, 568/660; 424/299, 341, 346

[56] References Cited

FOREIGN PATENT DOCUMENTS 2700340 7/1977 Fed. Rep. of Germany .

*Primary Examiner*—Howard T. Mars
*Assistant Examiner*—Vera C. Clarke
*Attorney, Agent, or Firm*—Ladas & Parry

[57] ABSTRACT

The present invention relates to novel compounds of the general formula

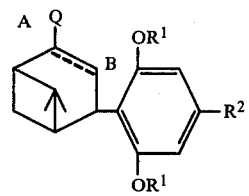

wherein $R^1$ is —H or —CO—alk, wherein alk is lower alkyl of 1 to 5 carbon atoms; $R^2$ is 1,1-dimethylheptyl or 1,2-dimethylheptyl, Q is —CH₃ when A———B is a single bond, and Q is —CH₂OR⁴ when A———B is a double bond, and $R^4$ is —H or —CO—alk where alk is lower alkyl of 1 to inclusive 5 carbon atoms.

The invention relates both to the isomeric mixtures and to the individual isomers of the above compounds. Furthermore the invention relates to pharmaceutical compositions containing a compound defined above as active ingredient. The pharmaceutical compositions are of value as central nervous system depressants, as sedatives, as tranquilizers, as anticonvulsant agents, as effective agents against migraine, for the treatment of glaucoma, as antidiarrheal agents and as antiinflammatory agents. The invention also relates to a process for the production of the above compounds and pharmaceutical compositions.

12 Claims, No Drawings

PINENE DERIVATIVES AND PHARMACEUTICAL COMPOSITIONS CONTAINING THE SAME

FIELD OF THE INVENTION

There are provided novel derivatives of resorcinol, substituted at C-2 with a pinane derived moiety. There are also provided novel pharmaceutical compositions which have interesting useful pharmacological properties. Some of the compounds are valuable analgesics, some are also tranquilizers and have a central nervous system depressant effect. Certain of the compounds of the invention may have an anticonvulsant, antimigraine, anti-glaucoma, anti-nausea, anti-ulcer, antidiarrheal and anti-inflammatory activity. Compounds of the present invention are also useful as intermediates for the preparation of pharmaceutically active compounds. Other and further aspects of the pesent invention will become apparent hereinafter. The invention also relates to a process for the production of the novel compounds and compositions of matter.

STATE OF THE PRIOR ART

The (—) form of the compound

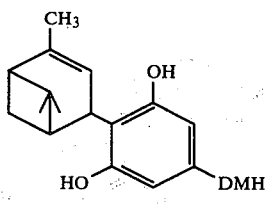

is known, the (+) form is mentioned as intermediate in copending patent application Ser. No. 48,824. Nothing is known about the biological activity of either of the above.

SUMMARY OF THE INVENTION

According to the present invention there are provided novel compounds of the general formula

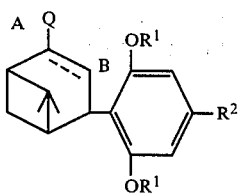

wherein
$R^1$ is —H or —CO—alk, wherein alk is lower alkyl of 1 to 5 carbon atoms;
$R^2$ is 1,1-dimethylheptyl or 1,2-dimethylheptyl,
Q is —CH$_3$ when A—B is a single bond, and
Q is —CH$_2$OR$^4$ when A—B is a double bond, and $R^4$ is —H or —CO—alk where alk is lower alkyl of 1 to inclusive 5 carbon atoms,
novel pharmaceutical compositions which contain the above as active ingredients and a process for the production of the above novel compounds and novel compositions.

In the above formula lower alkyl designates methyl, ethyl, propyl, isopropyl, butyl, isobutyl and pentyl.

Preferred compounds are compounds wherein A—B is a double bond, Q is —CH$_2$OH and $R^2$ is either 1,1-dimethylheptyl or 1,2-dimethylheptyl.

The compounds defined above exist as stereoisomers due to the presence of several centers of assymetry. The present invention relates to the isomeric mixtures and also to the individual isomers. The preparation of the isomers or the resolution of the isomeric mixtures can be effected by conventional means, as will be evident to those versed in the art. The novel processes for the production of compounds of the above formula are given hereinafter. The novel compounds of the present invention are valuable intermediates in organic synthesis. Compounds of the present invention are active ingredients of pharmaceutical compositions. Compounds of the present invention are effective analgesics. Some of them, i.e. compounds defined above as preferred compounds, have an analgesic activity at levels of the same order as morphine.

Compounds of the present invention have central nervous system depressant, sedative and tranquilizing activity. Some of the compounds have an anticonvulsive, an antimigraine, anti-glaucoma, anti-nausea, anti-ulcer, anti-diarrheal and an anti-inflammatory effect.

The intestinal motility data in the Table are relevant to the anti-diarrheal activity of the compounds of the invention. The ring test is a measure of psychotropic activity. The intestinal motility test was according to Chesher et al., Brit. J. Pharmacol. 49, 588 (1973) and the ring test was carried out according to Pertwee, Brit. J. Pharmacol. 46 753 (1972).

The compounds of the present invention are administered for the above defined purposes in conventional pharmaceutical forms, with the required diluents, excipients etc. They can be administered by any of the conventional routes. The dosage varies from 1 mg to about 100 mg per day, in one or in divided doses.

The novel compounds of the present invention are obtained by preparing a suitably substituted pin-2-ene compound with a 5-alkyl resorcinol and reacting the resulting intermediate to obtain the desired final product.

According to one reaction sequence (illustrated in Reaction Scheme I), a pin-2-ene compound substituted at the 10-position by a lower alkyl-ester group is oxidized to give the corresponding 4-oxo derivative III, which is reduced to the corresponding 4-hydroxy compound IV, which is reacted with an 5-alkyl-resorcinol substituted at the 5-position with a 1,1-dimethylheptyl (1,1-DMH) or a 1,2-dimethylheptyl (1,2-DMH) group to give a 4-trans-[2-(5-alkyl-resorcinol)]-10-hydroxy-pin-2-ene esterified at the 10-position with a lower alkyl group (VI), which ester group is converted, if desired, to the corresponding 10-ol (VII) which can be esterified, if desired, to the corresponding triester (VIII). The monoester VI can also be esterified to the triester (VIII) which, if desired is reduced to the corresponding triol (VII).

The esterified compound II can be oxidized to the 4-oxo derivative (III) by means of sodium chromate, which can be reduced to the 4-hydroxy compound (IV) by means of lithium aluminum tri-t-butyloxy hydride, which latter can be condensed with the 5-alkyl resorcinol under conditions of acid catalysis, such as under catalysis by means of p-toluene sulfonic acid, to give the esterified compound (VI) which is converted to the 10-hydroxy derivative (VII) by means of lithium aluminum hydride reduction. As set out in Reaction Scheme II a trans-[2-(5-alkyl-resorcinol)]-pin-2-ene compound (IX) can be catalytically reduced to a 4-trans-[2-(5-alkyl-resorcinol)] pinane (X).

In reaction scheme I, in reactions 1,2,3 and 4, $R^4$ cannot be hydrogen.

The analgetic activity was tested by the acetic acid induced writhing test (Sofia et al., *J. Pharmacol.Expt.-Therap.* 18, 646, 1973), by the tail flick test (Grotto et al., *Arch Intern.Pharmacodyn.* 170, 257, 1967) and by the foot pressure test (Randall and Selito, *Arch, Int. Pharmacodyn.* 409, 1957). The central nervous system action was tested by the mouse ring test (Pertwee, *Brit. J. Pharmacol.* 46, 753, 1972).

The invention is illustrated with reference to the following Examples, which are to be construed in an illustrative and non-limitative manner.

Scheme I*

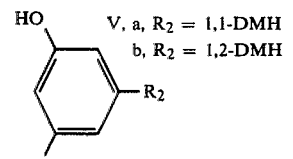

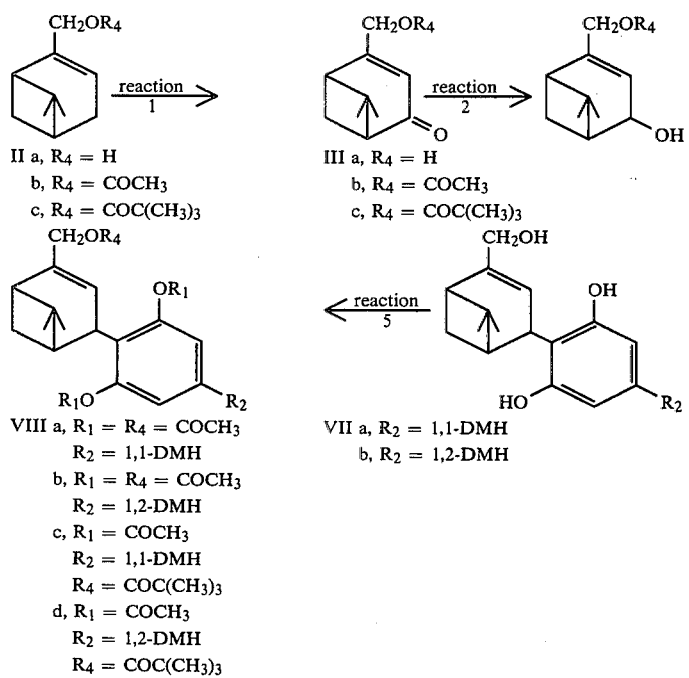

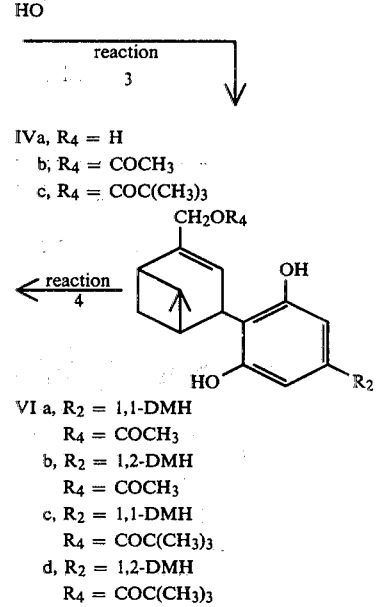

In reactions 1,2,3, $R_4$ cannot be H

Scheme II*

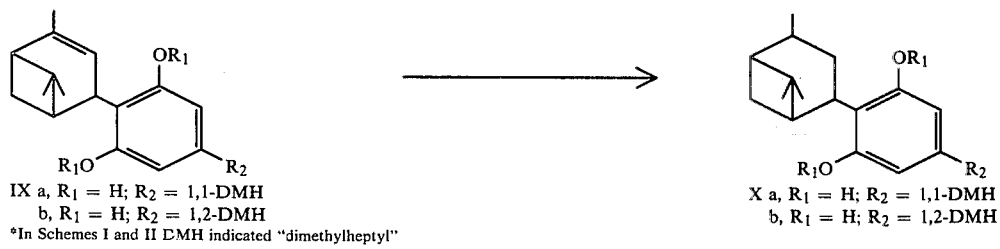

*In Schemes I and II DMH indicated "dimethylheptyl"

TABLE I

| | Analgesic tests | | |
|---|---|---|---|
| Material | Mouse writhing $ED_{50}$mg/kg | Mouse tail flick $ED_{50}$mg/kg | Rat foot pressure $ED_{50}$mg/kg |
| VIa(+) | 10 | 30 | 35 |
| VIa(−) | 10 | 10 | 25 |
| VIb(+) | 10 | 30 | 35 |
| VIb(−) | 10 | 10 | 25 |
| VIc(+) | 10 | 30 | 30 |
| VIc(−) | <10 | 10 | 30 |
| VId(+) | 10 | 30 | 30 |
| VId(−) | <10 | 10 | 30 |
| VIIa(+) | 5 | 30 | 15 |
| VIIa(−) | 7 | 6 | 25 |
| VIIb(+) | 5 | 30 | 15 |
| VIIb(−) | 7 | 6 | 25 |
| VIIIa(+) | 18 | 50 | 50 |
| VIIIa(−) | 18 | 30 | 50 |
| VIIIb(+) | 10 | 50 | 50 |
| VIIIb(−) | 10 | 30 | 50 |
| VIIIc(+) | 25 | >50 | >50 |
| VIIIc(−) | 25 | >50 | >50 |
| VIIId(+) | 25 | >50 | >50 |
| VIIId(−) | 25 | >50 | >50 |
| Xa(+) | 15 | ~50 | ~50 |
| Xa(−) | 9 | ~50 | ~50 |

TABLE I-continued

| | Analgesic tests | | |
|---|---|---|---|
| Material | Mouse writhing ED$_{50}$mg/kg | Mouse tail flick ED$_{50}$mg/kg | Rat foot pressure ED$_{50}$mg/kg |
| Xb(+) | 6 | ~50 | ~50 |
| Xb(−) | 6 | ~50 | ~50 |

*The signs (+) or (−) indicate optical rotation of the material

EXAMPLE 1

Myrtenol (IIa) $[\alpha]_D$−47.5° (in ethanol) was esterified to myrtenyl pivalate (IIc) $[\alpha]_d$−32°, with p valoyl chloride in pyridine by keeping the mixture at room temperature for 24 hr, extraction with ether, washing with dilute HCl and evaporation of the solvent. Anhydrous sodium chromate (54 g) was added to a solution of myrtenyl pivalate (IIc) (34 g) in acetic acid (190 ml) and acetic anhydride (85 ml). The mixture was stirred at 35° under nitrogen for 72 hr, cold water was added and the mixture was extracted with ether. The organic layer was washed with an aqueous solution of sodium hydrogen carbonate, dried and evaporated. Chromatography on silica gel (for dry column) (elution with 30% ether light petroleum) gave 4-oxo-myrtenyl pivalate (IIIc) (14 gr), $[\alpha]_D$−155° (in ethanol); NMR spectrum in (CDCl$_3$) 5.84, 4.72, 1.52, 1.24, 1.02; UV spectrum 250 nm ($\epsilon$, 6000).

Lithium aluminum tri-tert-butyloxy hydride (8.4 gr) in dry tetrahydrofuran (50 ml) was added dropwise to 4-oxo-myrtenyl pivalate (IIIc) (0.75 g), $[\alpha]_D$−155° in the same solvent (130 ml). The mixture was stirred under nitrogen for 3 h at 0° C., acetic acid (3 ml) and water (50 ml) were added dropwise. The mixture was stirred for 0.5 hr and was then filtered and washed with chloroform. The chloroform solution was washed with water, dried and evaporated. 4-Hydroxy-myrtenyl pivalate (IVc) (0.736 g) thus obtained showed one spot on tlc; NMR spectrum in (CDCl$_3$) 5.59, 4.43, 1.30, 1.14, 1.01. 4-Hydroxy myrtenyl pivalate (IVc) (1.5 g) in dry CH$_2$Cl$_2$ (60 ml) was added over a period of 30 min to a solution of 5-(1,2-dimethylheptyl) resorcinol (Vb) (1.44 g) and p-toluene sulphonic acid (0.48 g) in CH$_2$Cl$_2$ (240 ml). The solution was left at room temperature for further 90 min, washed with a saturated solution of sodium bicarbonate, dried and evaporated. The oil obtained (1.9 g) was chromatographed on a silica gel column. Elution with petroleum ether-ether in ratio of 8:1 gave 4-trans-[2-(5-(1,2-dimethylheptyl)-resorcyl)]-10-hydroxy-pin-2-ene, 10 pivalate (VId) (1.55 g), $[\alpha]_D$−85°; NMR spectrum (in CDCl$_3$) 6.19, 6.01, 4.56, 4.02, 2.30, 1.33, 1.23, 0.97, 0.86, 0.78.

Acetylation with acetic anhydride and pyridine led to 4-trans-[2-(5-(1,2-dimethylheptyl)-resorcyl diacetate)]-10-hydroxy-pin-2-ene-10-pivalate (VIIId) $[\alpha]_D$−65° (in ethanol). NMR spectrum (in CDCl$_3$) 6.70, 5.66, 4.52, 3.74, 2.22, 1.29, 1.26, 1.21, 0.94.

EXAMPLE 2

Anhydrous sodium chromate (3.2 g) was added to a solution of (−) myrtenyl acetate (IIb) (2 g), $[\alpha]_D$−41.7°, in acetic acid (24 ml) and acetic anhydride (12 ml). The mixture was stirred at 35° under nitrogen for 72 hrs, cold water was added and the mixture was extracted with ether. The organic layer was washed with an aqueous solution of sodium hydrogen carbonate, dried and evaporated. Chromatography on silica gel (elution with 30% ether in petroleum ether) gave 4-oxo-myrtenyl acetate (IIIb) (620 mg), $[\alpha]_D$−180° (in ethanol); NMR spectrum (in CDCl$_3$) 1.02, 1.52, 2.1, 4.7, 5.85; UV spectrum 247 nm ($\epsilon$, 7453).

Lithium aluminum tri tert butyloxy hydride (0.84 gr) in dry tetrahydrofuran (5 ml) was added to 4-oxo-myrtenyl acetate (IIIb) (62 mg), $[\alpha]_D$−180°. The mixture was stirred for 3 hrs at 0°. Acetic acid (0.3 ml) and water (0.5 ml) were added. The reaction was stirred for a further hour. The mixture was filtered, the organic solution was dried and evaporated. The 4-hydroxy-myrtenyl acetate (IVb) (52 mg) obtained had the following NMR spectrum (in CCl$_4$) 1.03, 1.38, 2.02, 4.41 (3 protons $\alpha$ to oxygen), 5.56. 4-Hydroxy myrtenyl acetate (IVb) (0.523 g) in dry CH$_2$Cl$_2$ (30 ml) was added over a period of 30 min to a solution of 5-(1,1-dimethylheptyl) resorcinol (Va) (0.600 g) and p-toluene sulphonic acid (0.220 g) in CH$_2$Cl$_2$ (120 ml). The solution was left at room temperature for further 90 min, washed with a saturated solution of sodium bicarbonate dried and evaporated. The residual gum (VIa) was dissolved in pyridine (5 ml) and acetic anhydride (5 ml) and was left at room temperature overnight. The solution was poured into ice-cold water. The mixture was extracted with ether. The ethereal solution was washed with a solution of HCl (1 N), then with a sodium bicarbonate solution, dried and evaporated. The oil obtained was chromatographed on silica gel (for dry column). Elution with petroleum ether-ether in a ratio of 8:1 gave 4-trans-[2-(5-(1,1-dimethylheptyl)-resorcyl)]-10-hydroxy-pin-2-ene, triacetate (VIIIa) (0.491 g), $[\alpha]_D$−72°. NMR spectrum (in CDCl$_3$): 6.83, 5.66, 4.52, 3.66, 2.23, 2.06, 1.30, 0.92.

EXAMPLE 3

Compound (VIIIa) (0.220 g), $[\alpha]_D$−72° in dry ether (2 ml) was added to a suspension of lithium aluminum hydride (0.2 g) in ether (25 ml). The mixture was stirred for 2 hrs at room temperature. The excess of reagent was destroyed with saturated solution of sodium sulphate and HCl (1 N) and the mixture was extracted with ether and washed with a solution of sodium bicarbonate. The extract was dried and evaporated to give 4-trans-[2-(5-(1,1-dimethylheptyl)-resorcyl)]-10-hydroxy-pin-2-ene (VIIa) (0.135 g), $[\alpha]_D$−66.6°. NMR spectrum (in CDCl$_3$) 6.25, 6.08, 4.07, 2.33, 1.24, 1.11, 0.89.

EXAMPLE 4

Myrtenyl acetate (IIb), $[\alpha]_D$+44.2° was converted via 4-oxo-myrtenyl acetate (IIIb), $[\alpha]_D$+177°, into 4-hydroxy-myrtenyl acetate (IVb) as described in Example 2.

4-Hydroxy-myrtenyl acetate (IVb), thus obtained (0.523 g) was condensed with 5-(1,2-dimethylheptyl)-resorcinol (Vb) (600 mg) and then acetylated exactly as described for the 1,1-dimethylheptyl isomer (Va) described in Example 2. 4-Trans-[2-(5-(1,2-dimethylheptyl-resorcyl)]-10-hydroxy-pin-2-ene, triacetate (VIIIb) (0.502 g), $[\alpha]_D$+81°. NMR spectrum in CDCl$_3$: 0.92, 1.30, 2.06, 2.24, 3.66, 4.52, 5.66, 6.70.

EXAMPLE 5

4-Trans-[2-(5-(1,2-dimethyl)-resorcyl)]-10-hydroxy-pin-2-ene triacetate (VIIIb) (0.220 g), $[\alpha]_D$+81° was reduced with lithium aluminum hydride as described in Example 3. 4-Trans[2-(5-(1,2-dimethylheptyl)-resorcyl)]-10-hydroxy-pin-2-ene (VIIb) (0.152 g), $[\alpha]_D$+82° was obtained. NMR spectrum (in CDCl$_3$) 0.98, 1.20, 1.35, 2.30, 4.16, 6.00, 6.22.

EXAMPLE 6

4-Trans-[2-(5-(1,1-dimethylheptyl)-resorcyl)]-pin-2-ene (IXa) (600 mg) $[\alpha]_D+98$ was reduced in EtOH over 10% palladium on charcoal catalyst until the uptake of hydrogen had ceased. The catalyst was filtered off and the solvent was removed under vacuum. 4-Trans-[2-(5-(1,1-dimethylheptyl)-resorcyl)]-pinane (Xa) (550 mg) was obtained. It showed only one peak on tlc, $[\alpha]_D+3$ (in ethanol). NMR spectrum (in CDCl$_3$) 6.33, 4.83, 1.30, 1.26, 1.16, 1.00, 0.93, 0.85.

EXAMPLE 7

4-Hydroxy-myrtenylacetate (IVb) (see Example 4) prepared from myrtenyl acetate (IIb), $[\alpha]_D+39°$, via 4-oxomyrtenyl acetate (IIIb) $[\alpha]_D+177°$ was condensed with 1,1-dimethylheptyl resorcinol and the reaction product was acetylated and purified exactly as described in Example 2 (which deals with the corresponding compounds but with negative rotations). 4-Trans-[2-(5-(1,1-dimethylheptyl)-resorcyl)]-10-hydroxy-pin-2-ene triacetate (VIIIa) thus obtained showed $[\alpha]_D+74°$ (ethanol), NMR spectrum (CDCl$_3$) equivalent to that of VIIIa with negative rotation described in Example 2.

Compound VIIIa, $[\alpha]_D+74°$ was reduced with lithium aluminum hydride exactly as described in Example 3 for the corresponding compound with negative rotation. 4-Trans-[2-(5-(1,1-dimethylheptyl)-resorcyl)]-10-hydroxy-pin-2-ene (VIIa) showed $[\alpha]_D+75.3°$ and had an NMR spectrum identical to that of VIIa (with negative rotation) described in Example 3.

EXAMPLE 8

4-Hydroxy-myrtenyl acetate (IVb) was prepared from myrtenyl acetate (IIb), $[\alpha]_D-41.7°$ via 4-oxomyrtenyl acetate (IIIb) $[\alpha]_D-180°$ as described in Example 2.

Compound IVb (0.575 g) in dry CH$_2$Cl$_2$ (35 ml) was added over a period of 30 min to a solution of 5-(1,2-dimethyl heptyl)-resorcinol (Vb) (0.660 g) and p-toluene sulphonic acid (0.240 g) in CH$_2$Cl$_2$ (130 ml). The solution was left at room temperature for further 90 min, washed with a saturated solution of sodium bicarbonate, dried and evaporated. The residual gum was dissolved in pyridine (7 ml) and acetic anhydride (5 ml) and was left at room temperature overnight. The solution was worked up as described in Example 2. The oil obtained was chromatographed on silica gel. Elution with petroleum ether-ether in a ratio of 8:1 gave 4-trans-[2-(5-(1,2-dimethylpheptyl))-resorcyl)-10-hydroxy-pin-2-ene, triacetate (VIIIb) (0.550 g), $[\alpha]_D-74°$; NMR spectrum (in CDCl$_3$): 0.92, 1.30, 2.06, 2.24, 3.66, 4.52, 5.66, 6.70.

Compound (VIIIb) (0.220 g) was reduced with lithium aluminum hydride as described in Example 3. 4-Trans-[2-(5-(1,2-dimethyheptyl)-resorcyl)]-10-hydroxy-pin-2-ene (VIIb) (0.160 g) $[\alpha]_D-68°$ was obtained. NMR spectrum (in CDCl$_3$): 0.98, 1.24, 1.36, 2.33, 4.16, 6.00, 6.25.

EXAMPLE 9

4-Trans-[2-(5-(1,2-dimethylheptyl)-resorcyl)]-pin-2-ene (IXb) (660 mg), $[\alpha]_D+82°$ was reduced exactly as described in Example 6. 4-Trans-[-(5-(1,2-dimethylheptyl)-resorcyl)]-pinane (Xb) (610 mg) $[\alpha]_D+1°$ was obtained. It had an NMR spectrum (in CDCl$_3$) 0.78-1.3 mult., 1.56-2.42 mult., 5.0 (s), 6.17 (s)

EXAMPLE 10

Compound IX a $[\alpha]_D-71°$ was converted into 4-trans-[2-(5-(1,1-dimethylheptyl)-resorcyl)]-pinane (Xa) $[\alpha]_D-2°$ exactly as described in Example 6. It had an identical NMR spectrum as the corresponding isomer with a positive rotation.

We claim:

1. A compound of the general formula

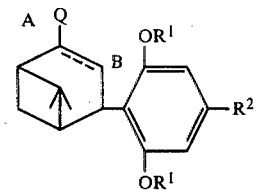

wherein

R$^1$ is hydrogen or —CO—alk, where alk is lower alkyl of up to 5 carbon atoms,

R$^2$ is 1,1-dimethylheptyl or 1,2-dimethylheptyl, with the proviso that:

when A—B is a single bond Q is —CH$_3$, and when A—B is a double bond, Q is —CH$_2$OR$^4$ and R$^4$ is hydrogen or —CO—alk where alk is lower alkyl of up to 5 carbon atoms.

2. A compound according to claim 1, wherein A—B is a double bond and Q is —CH$_2$OH, wherein R$^2$ is selected from the group consisting of 1,1-dimethylheptyl and 1,2-dimethylheptyl.

3. A compound according to claim 1, wherein R$^1$ is —CO—alk, and "alk" is methyl, ethyl, propyl, isopropyl, butyl, isobutyl or pentyl.

4. A compound according to claim 1, wherein alk in R$^4$ is selected from the group consisting of ethyl, methyl, propyl, isopropyl, butyl, isobutyl and pentyl.

5. A racemic mixture of compounds according to claim 1.

6. The individual optical isomers of the compounds according to claim 1.

7. A compound according to claim 1, wherein R$^1$ is hydrogen.

8. An analgesic composition comprising an analgesically effective amount of the compound of claim 1 together with a pharmaceutically acceptable carrier.

9. A central nervous system depressant composition comprising an anti-depressant amount of the compound of claim 1 together with a pharmaceutically acceptable carrier.

10. A sedative composition comprising a sedative amount of the compound of claim 1 together with a pharmaceutically acceptable carrier.

11. A tranquilizer composition comprising a tranquilizing amount of the compound of claim 1 together with a pharmaceutically acceptable carrier.

12. A composition according to claim 8 wherein A———B is a double bond, Q is —CH$_2$OH and R$^2$ is selected from the group consisting of 1,1-dimethylheptyl and 1,2-dimethylheptyl.

* * * * *